(12) United States Patent
Leinen

(10) Patent No.: US 7,802,764 B2  
(45) Date of Patent: Sep. 28, 2010

(54) ADJUSTABLE WHEELED IV STAND

(76) Inventor: Chris M. Leinen, 1872 Happy Valley Rd., Santa Rosa, CA (US) 95409

( * ) Notice: Subject to any disclaimer, the term of this patent is extended or adjusted under 35 U.S.C. 154(b) by 0 days.

(21) Appl. No.: 11/803,632

(22) Filed: May 14, 2007

(65) Prior Publication Data

US 2008/0283692 A1 Nov. 20, 2008

(51) Int. Cl.
   *A47K 1/04* (2006.01)
   *F16M 11/38* (2006.01)
(52) U.S. Cl. .............. 248/129; 248/170; 248/188.2
(58) Field of Classification Search ........... 248/121, 248/125.1, 127, 128, 129, 125.9, 170, 188.2; 5/87.1, 507.1, 658, 503.1, 81.1 R, 612; 280/47.12, 280/47.16
See application file for complete search history.

(56) References Cited

U.S. PATENT DOCUMENTS

| | | | |
|---|---|---|---|
| 2,303,978 A | 11/1940 | Biberman | |
| 3,064,932 A | 11/1962 | Holderman | |
| 4,062,372 A | 12/1977 | Slusher | |
| 4,183,579 A | 1/1980 | Gonzalez y. Rojas | |
| 4,332,378 A | 6/1982 | Pryor | |
| 4,381,690 A | 5/1983 | Kimble | |
| 4,744,536 A * | 5/1988 | Bancalari ................. | 248/125.8 |
| 4,807,837 A | 2/1989 | Gawlik et al. | |
| 4,832,294 A | 5/1989 | Eidem | |
| 4,892,279 A * | 1/1990 | Lafferty et al. ............ | 248/125.8 |
| 4,932,719 A | 6/1990 | Rojas | |
| 5,072,910 A * | 12/1991 | May ........................... | 248/170 |
| 5,241,870 A * | 9/1993 | Holt .......................... | 73/866.5 |
| 5,337,992 A | 8/1994 | Pryor et al. | |
| 5,344,169 A * | 9/1994 | Pryor et al. ................. | 280/79.3 |
| 5,458,305 A | 10/1995 | Woodward | |
| 5,551,105 A | 9/1996 | Short | |
| 5,556,065 A * | 9/1996 | Wadley ...................... | 248/129 |
| 5,704,577 A | 1/1998 | Gordon | |
| 5,772,162 A | 6/1998 | Lin | |
| 5,890,687 A | 4/1999 | Pryor et al. | |
| D457,239 S * | 5/2002 | Kunik ....................... | D24/128 |
| 6,454,228 B1 | 9/2002 | Bosnakovic | |
| 6,688,634 B2 * | 2/2004 | Noffsinger ................. | 280/651 |
| 2006/0202092 A1* | 9/2006 | Johnson ..................... | 248/146 |
| 2007/0023587 A1* | 2/2007 | Eggleston et al. ......... | 248/125.8 |
| 2008/0156946 A1* | 7/2008 | Schmutzer et al. ....... | 248/125.8 |
| 2008/0283692 A1* | 11/2008 | Leinen ..................... | 248/125.8 |

FOREIGN PATENT DOCUMENTS

EP 0 015 034 9/1980

* cited by examiner

*Primary Examiner*—Amy J Sterling
*Assistant Examiner*—Tan Le
(74) *Attorney, Agent, or Firm*—Craig M. Stainbrook; Stainbrook & Stainbrook, LLP

(57) ABSTRACT

An adjustable IV stand has an adjustable support, which can be adjusted from a first compact configuration to a second expanded configuration that provides increased stability and a stand suitable for use to assist an ambulatory patient with walking.

8 Claims, 5 Drawing Sheets

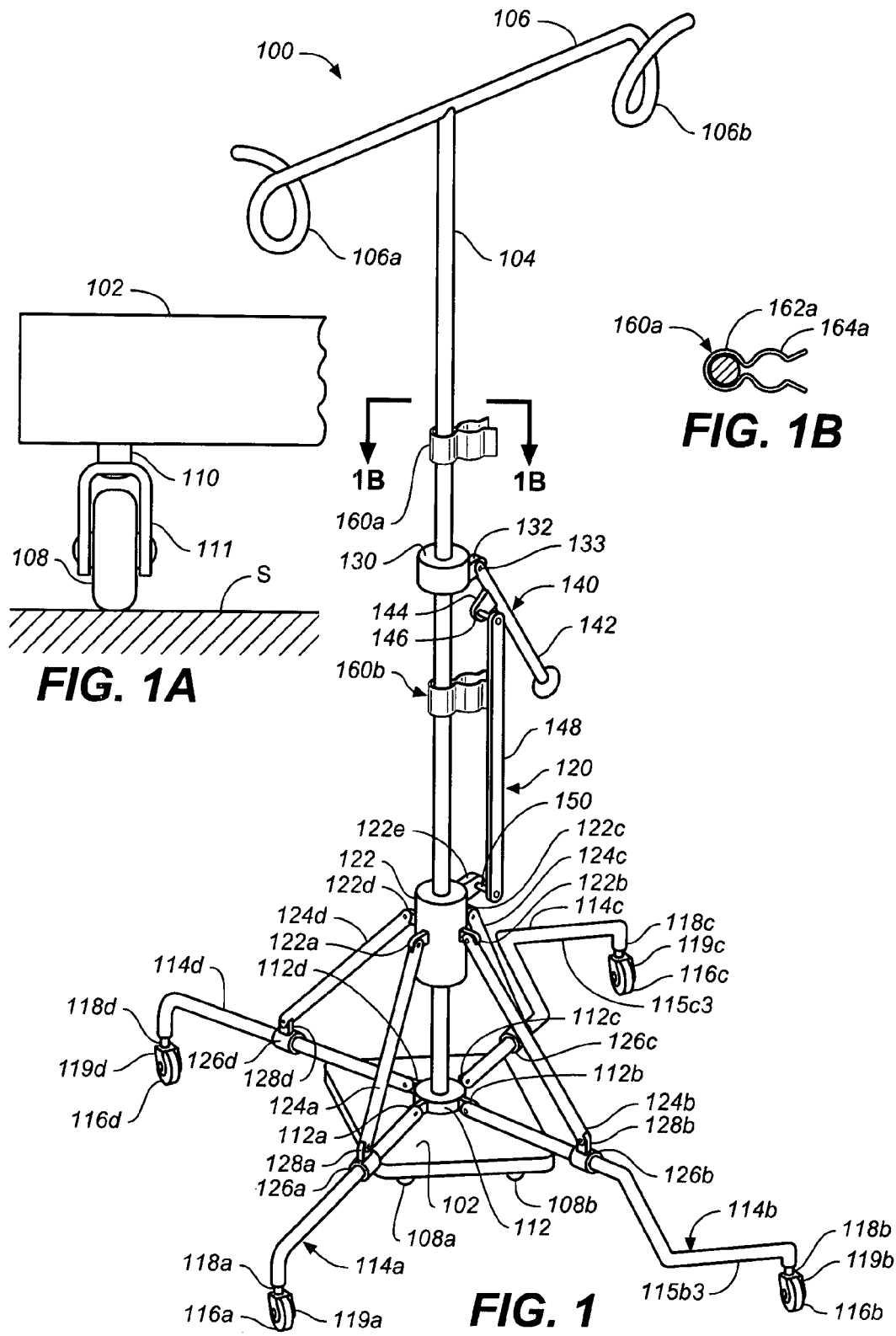

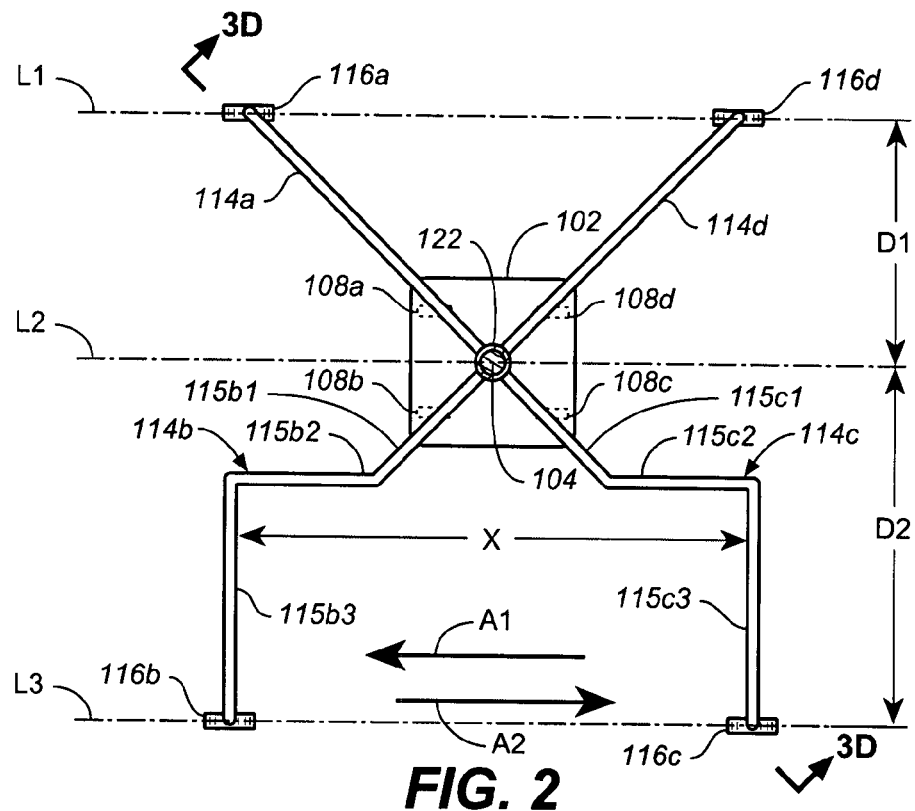
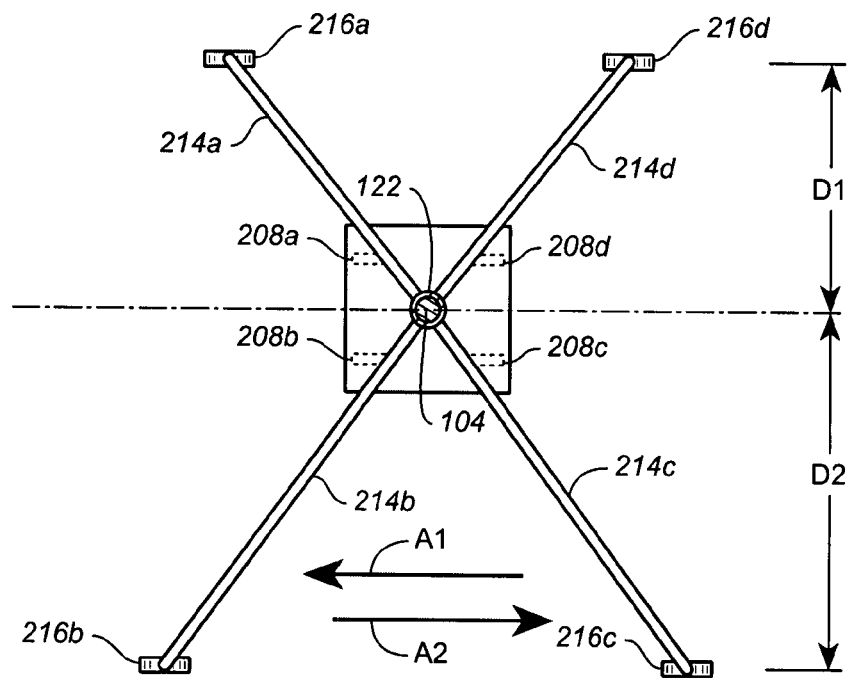

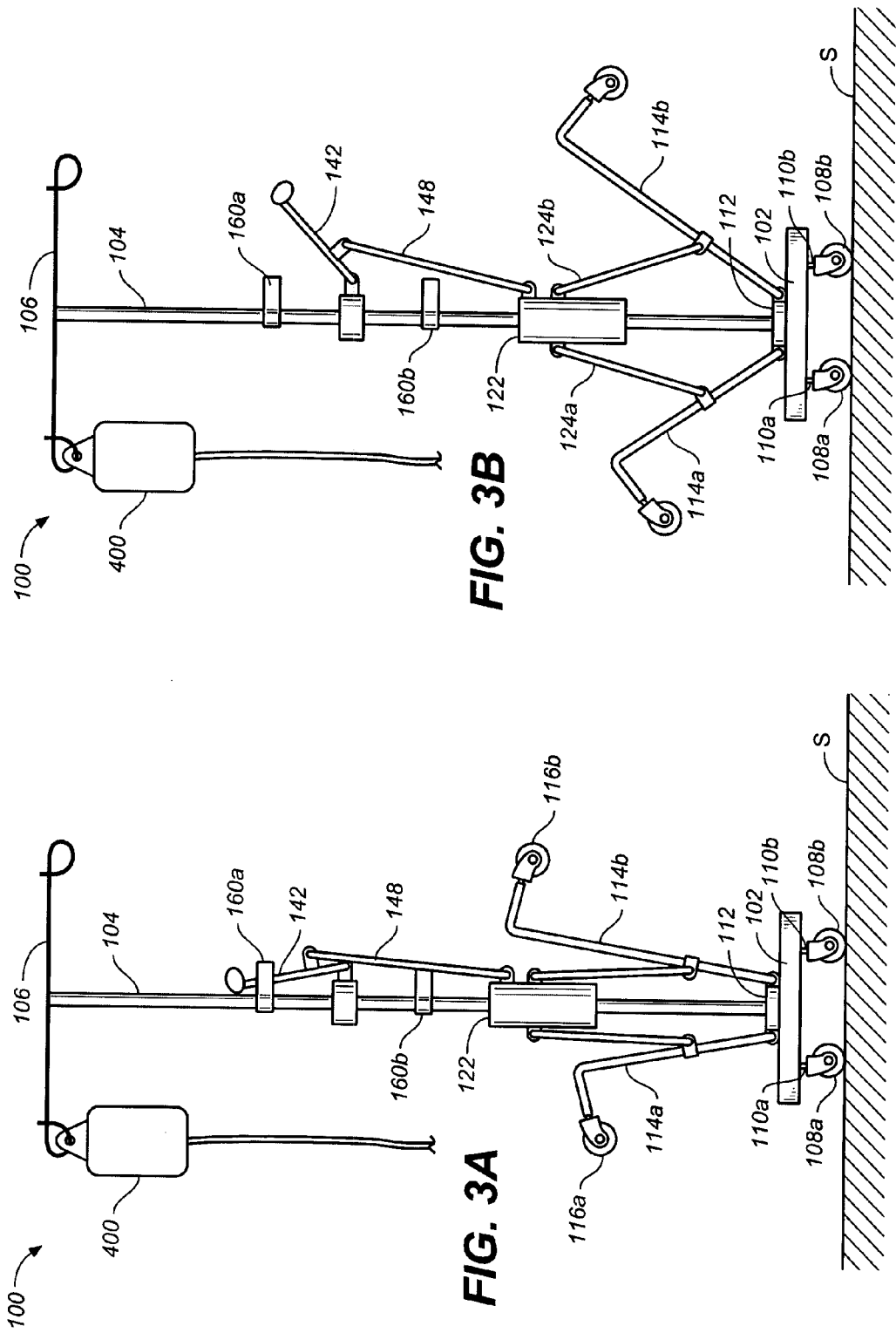

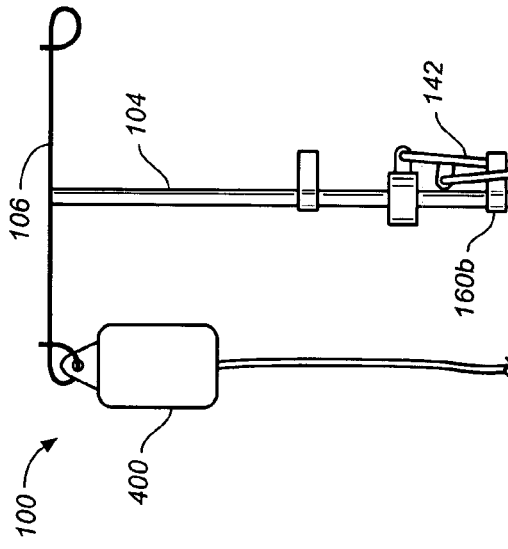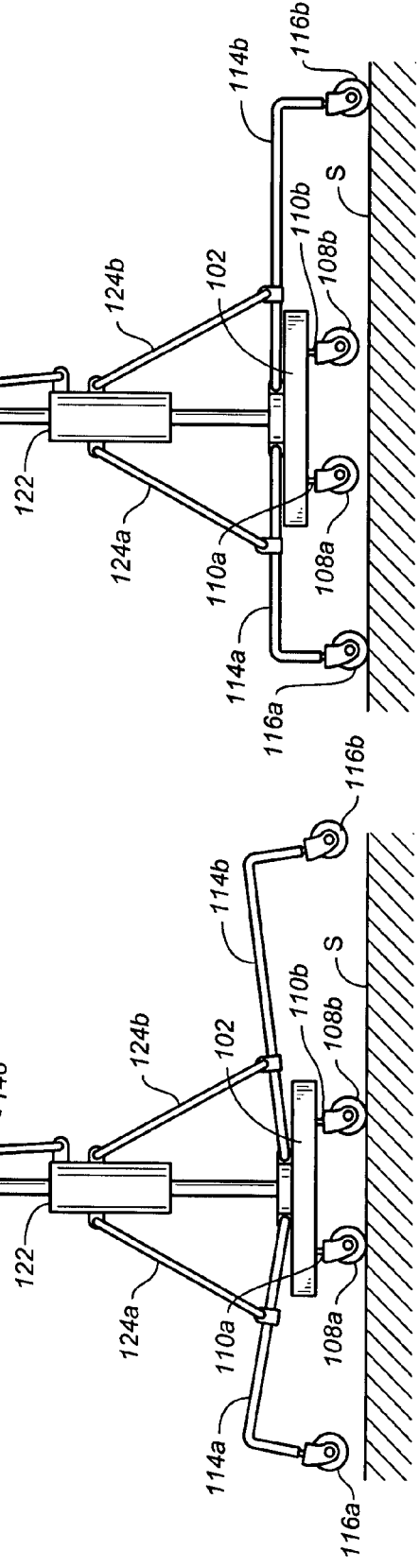

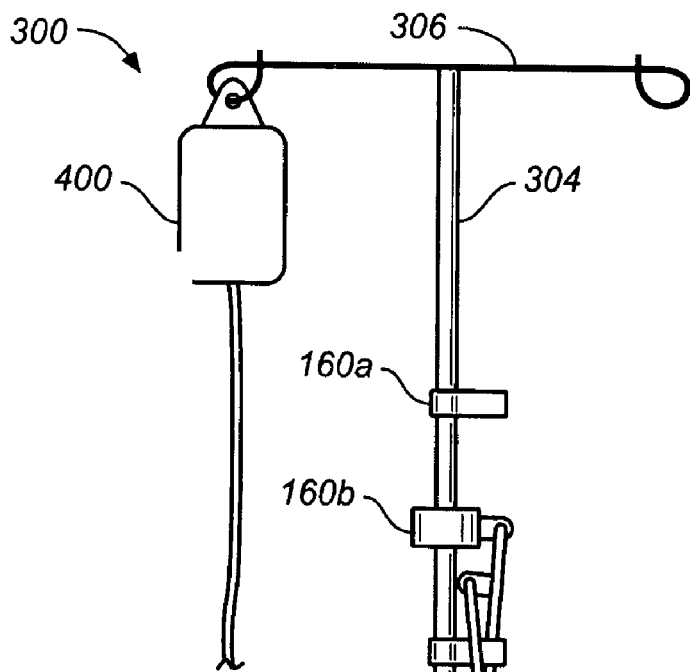
FIG. 4
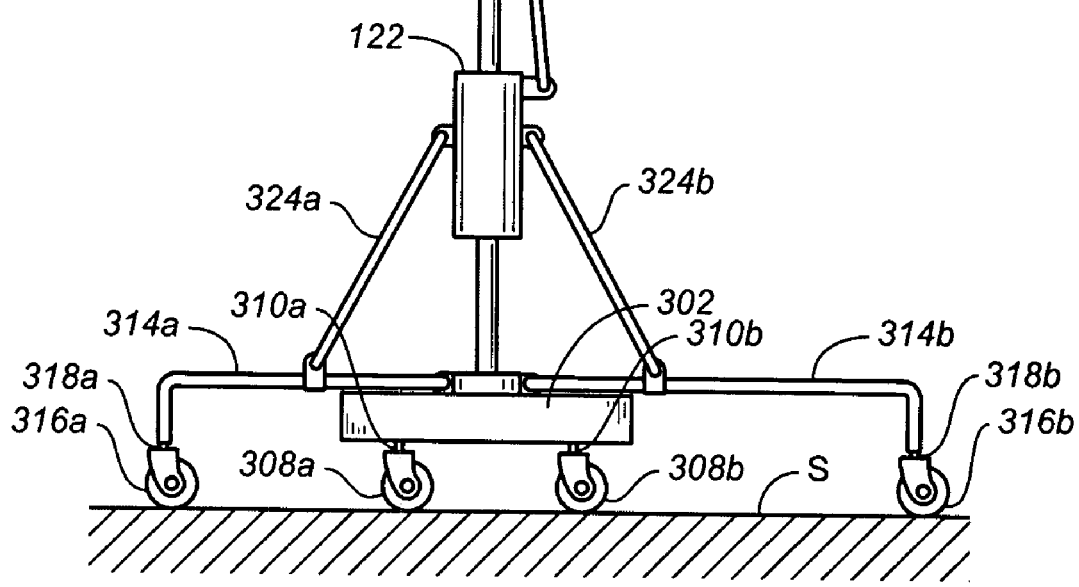

ADJUSTABLE WHEELED IV STAND

FIELD OF THE INVENTION

The invention relates to intravenous (IV) stands, and more specifically to wheeled IV stands.

BACKGROUND OF THE INVENTION

Wheeled IV stands are widely used to hang IV bags or bottles at a level to allow gravity assisted flow to a patient or to an intermediate device such as an IV pump. Examples of wheeled IV stands are described in U.S. Pat. No. 4,832,294 to Eidem and entitled Portable I.V. Stand, U.S. Pat. No. 5,458,305 to Woodward and entitled Portable Intravenous Support Stand and U.S. Pat. No. 5,772,162 to Lin and entitled Drop-Bottle Stand. And examples of foldable wheeled IV stands are described in U.S. Pat. No. 4,744,536 to Bancalari and entitled Collapsable Pole and Stand Combination and U.S. Pat. No. 4,892,279 to Lafferty et al. and entitled Fully Portable Medical I.V. Equipment Stand/Pole.

Wheeled stands have evolved to include support brackets for ambulatory patients or mounting brackets to support additional equipment such as oxygen bottles. U.S. Pat. No. 4,332,378 to Pryor, et al. and entitled Ambulatory Patient Support Stand, describes a wheeled IV stand with a horizontal patient gripping element when the stand is used as a walker. The gripping element is mounted low on the vertical support of the IV stand and the stand has a low center of gravity. These aspects are stated to improve stability. U.S. Pat. No. 5,337,992 to Pryor et al. and entitled Support Device for Ambulatory Patient describes a support for an ambulatory patient that mounts on a vertical pole of a wheeled IV stand. U.S. Pat. No. 5,551,105 to Short and entitled Apparatus Combining Overbed Table, IV Stand, Walker, and Seat and U.S. Pat. No. 5,704,577 to Gordon and entitled Walker-IV Stand Coupler describe apparatus combining an IV stand and walker. These apparatus, however, require a substantial amount of space.

U.S. Pat. No. 5,890,687 to Pryor et al. and entitled Foldable Wheeled Stand describes a foldable wheeled stand with a support handle to allow ambulatory patients to use the stand both for transport of necessary medical equipment including, IV fluid containers, and for ambulatory support. The stand is collapsible from an upright orientation in which all wheels are floor-engaging to a folded orientation in which the wheels lie closely alongside the support pole.

While the above features add functionality to IV stands, there remains a need to improve IV stands for use in different modalities.

SUMMARY OF THE INVENTION

In one embodiment according to the invention, an adjustable IV stand has an adjustable support, which can be adjusted from a first compact configuration to a second expanded configuration that provides increased stability and a stand suitable for use as a support to assist an ambulatory patient with walking.

In another embodiment according to the invention, an adjustable IV stand has an adjustable wheelbase, which can be expanded to provide increased stability and a stand suitable for use as a support to assist an ambulatory patient with walking.

In another embodiment according to the invention, an adjustable IV stand comprises a base member having a plurality of rotating wheels non-pivotally coupled thereto; a support pole for supporting an IV fluid container, the support pole having an upper end and a lower end, the lower end being coupled to and supported by the base member; and at least three swiveling wheels pivotally coupled to at least one of the support pole and the base member for adjustment between a raised position and a lowered position relative to the base member.

In another embodiment according to the invention, an adjustable IV stand comprises a base member having a plurality of wheels rotatably mounted thereto; a support pole for supporting an IV fluid container, the support pole having an upper end and a lower end, the lower end being coupled to and supported by the base member; an IV container support coupled to the pole for supporting at least one IV container; and a plurality of legs pivotally coupled to at least one of the support pole and the base member for adjustment between a raised position and a lowered position relative to the base member, each adjustable leg having a wheel rotatably coupled thereto.

In another embodiment according to the invention, a method of using an IV stand comprises adjusting an IV stand, which has a base member with a first group of wheels that are coupled to the base member and a second group of wheels that are adjustable in position, from a first configuration where the IV stand is self-supported on a floor in an upright position through the first group of wheels and the second group of wheels are in a raised, non-floor engaging position where they do not support the IV stand, to a second configuration where the second group of wheels are lowered to engage the floor and increase the IV stand support span in at least one direction; and using the IV stand, when in the second configuration and with an IV container supported thereby, as a support to assist an ambulatory patient with walking.

The above is a brief description of some deficiencies in the prior art and advantages of the present invention. Other features, advantages, and embodiments of the invention will be apparent to those skilled in the art from the following description and accompanying drawings, wherein, for purposes of illustration only, specific forms of the invention are set forth in detail.

BRIEF DESCRIPTION OF THE DRAWINGS

FIG. 1 is a perspective view an intravenous stand according to one embodiment of the invention.

FIG. 1A is an elevational view of one embodiment of a swiveling wheel suitable for use in the embodiment of FIG. 1.

FIG. 1B is a sectional view taken along line 1B-1B in FIG. 1.

FIG. 2 is a top view of the leg configuration shown in FIG. 1.

FIG. 2A is another embodiment according to the invention depicting a leg configuration variation where the view is similar to that illustrated in FIG. 2.

FIGS. 3A-3D diagrammatically illustrate use of the embodiment of FIG. 1 where FIG. 3A shows a side elevational view of the IV stand self-supported through a group of floor engaging wheels coupled to a base member and with its secondary wheels in a raised non-floor engaging position, FIG. 3B shows the secondary wheels being lowered, FIG. 3C shows the secondary wheels being further lowered, and FIG. 3D shows the secondary wheels fully lowered and engaging the floor to support the IV stand and the base member wheels lifted off the floor so as to be non-floor engaging wheels and the wheelbase expanded to increase stability of the stand.

FIG. 4 diagrammatically illustrates another embodiment where all of the base member wheels and the secondary wheels are floor engaging wheels when the IV stand is in an extended configuration with its wheelbase expanded.

DETAILED DESCRIPTION OF THE INVENTION

The following description will be made with reference to the drawings where when referring to the various figures, it should be understood that like numerals or characters indicate like elements. Further, before the present invention is described, it is to be understood that this invention is not intended to be limited to particular embodiments or examples described, as such may, of course, vary.

Referring to FIG. 1, one embodiment of a portable IV stand is shown and generally designated with reference numeral 100. IV stand 100 generally has a wheelbase that can be adjusted between first and second configurations to accommodate different modes of use. The wheelbase can be measured between any two wheels when in a first configuration and any two wheels when in a second configuration. For example, the wheelbase in FIG. 3A can be measured as the distance between the centers of wheels 108a and 108b and the wheelbase in FIG. 3D can be measured as the distance between centers of wheels 116a and 116b, which wheelbase is greater than that provided by wheels 108a and 108b. Alternatively, the configuration change can be described as an increase in the stand support span or area. In the expanded configuration illustrated in FIG. 3D, IV stand 100 provides increased stability to assist an ambulatory patient with walking, while the patient is coupled to an IV bag or container that can be hung from the IV stand.

Returning to FIG. 1, IV stand 100 generally includes a base member 102, and upright pole 104, an IV solution container support such as crossbar 106, a plurality of wheels 108a-d rotatably mounted to base member 102, and a plurality of wheels 116a-d arranged for movement between a floor engaging position to a retracted floor non-engaging position.

Upright IV solution container support pole 104 has an upper end and a lower end with the lower end of pole 104 being mounted to base member 102.

Although the IV solution container support pole 104 is shown as a single cylindrical element, other configurations and constructions can be used. For example, the IV solution container support pole can be a telescoping pole. An IV solution container support is coupled to support pole and can be in the form of crossbar 106, which is secured thereto, extends radially therefrom, and forms an angle of about 90 degrees therewith. Crossbar 106 includes one or more portions that are configured to support an IV solution container such as IV container 400 (see e.g., FIG. 3A). The portions can be loops or clips 106a and 106b or can have other suitable configurations.

Wheels 108a-d are swiveling wheels, which can have various mount configurations as would be apparent to one of ordinary skill in the art. One example is illustrated in FIG. 1B where a swivel mount comprises a post 110 rotatably mounted about its longitudinal axis to the underside of base member 102 and a bracket 111 mounted to post 110 and having a wheel 108 rotatably mounted thereto so that the wheel can rotate about its center axis for rolling and about the longitudinal axis of the post to change direction. Alternatively, post 110 can be fixedly secured to base member 102 and bracket 111 rotatably mounted to post 110 so that the bracket can rotate about the longitudinal axis of the post. It also should be understood that any other suitable commercially available swiveling wheel can be used.

One end of each leg 114a-d is pivotally coupled to base member 102. Each leg can be directly pivotally connected to base member 102 or pivotally coupled to base member 102 through a member secured or mounted to base member 102 such as hub 112 as shown in the exemplary embodiment. In this embodiment, pole 104 can be secured to the upper surface of hub 112 or hub 112 can be provided with a central bore in which pole 104 can be secured with any suitable means. Hub 112 has a plurality of brackets (e.g., 112a-d) extending therefrom and to which the ends of legs 116a-d are pivotally mounted.

Each of legs 114a-d has a swiveling wheel 116a-d coupled to an end portion thereof. Swiveling wheels 116a-d can be of the same construction as swiveling wheels 108a-d where post 118a corresponds to post 110 and brackets 119a-d correspond to bracket 111. Accordingly, swiveling wheels 116a-d swivel and rotate. It should be understood, however, that any other suitable commercially available swiveling wheel can be used. Further, although four pivotally mounted legs 114a-d are shown, three or more can be used. For example, legs 114a and 114d as shown in FIG. 2 can be replaced with a single pivoting leg having a swiveling well at its free end and its other end pivotally coupled to base 102 such that it extends between legs 114a and 114d, for example, in a direction generally parallel to a line that radially extends from hub 112 or pole 104. The single leg can be arranged to bisect the angle formed by legs 114a and 114d.

IV stand 100 also includes a mechanism to retract or move pivotally mounted legs 114a-d between raised and lowered positions. Although any suitable mechanism can be used, one mechanism, which generally is designated with reference numeral 120, is shown in the embodiment depicted in FIG. 1 for purposes of illustration. Mechanism 120 comprises a slide or cylindrical member 122, which is slidably mounted on pole 104. Cylindrical member or slide 122, which has a center bore that slidably receives pole 104, has a plurality of brackets 122a-d to which arms 124a-d are pivotally coupled. More specifically, each arm 124a-d has a first end pivotally coupled to a respective bracket 122a-d and a second end pivotally coupled to a respective leg 114a-d. Each leg can be provided with a coupling to pivotally couple a respective arm thereto. One coupling embodiment comprises a tube that is slidably coupled to a leg and a bracket extending from the tube to which an arm is pivotally coupled. Referring to FIG. 1, each arm is pivotally coupled to a respective leg through one of brackets 128a-d (bracket 128c is hidden from view, but is similar to brackets 128a, b & d), each of which extends from a tube 126a-d, which is slidably coupled to one of the legs. When slide 122 is raised, legs 114a-d and wheels 116a-d are raised and when slide 122 is lowered, legs 114a-d and wheels 116a-d are lowered.

Mechanism 120 further includes apparatus for raising and lowering slide 122. Although any suitable apparatus can be used, one embodiment of slide raising and lowering apparatus is shown for purposes of example. In the illustrative embodiment, a member 130, which can have any suitable configuration is fixedly secured to pole 130 and includes a bracket 132 extending therefrom. Control assembly 140 facilitates manual control of the position of slide 122 relative to fixed member 130. Control assembly 140 includes a lever arm 142 having one end pivotally coupled to bracket 132 and a bracket 144 extending from a portion thereof. The end of lever arm 142 that is pivotally coupled to bracket 132 can be configured in the form of a clevis with holes through which a pin, e.g., pin 133, that extends through bracket 132 can run. A similar clevis configuration can be used in any or all of the other arm or leg pivot couplings described herein, which as shown in FIG. 1, include similar pins. Any other suitable pivotal connection also can be used to pivotally couple lever arm 142 to bracket 132 or to form any of the other pivotal connections described herein. Link 148 has one end pivotally coupled to bracket 144 through pin 146 and a second end pivotally coupled to bracket 122e, which extends from and is fixedly secured to slide 122, through pin 150. When lever arm 142 is raised, slide 122 and wheels 116a-d are raised so as not to engage floor surface S (see e.g., FIG. 3A) and when lever arm 142 is lowered, slide 122 and wheels 116a-d are lowered so as to be floor surface engaging wheels (see e.g., 3D).

IV stand 100 can be provided with locking mechanisms to lock lever arm in a raised or lowered position. Referring to FIG. 1, locking mechanism 160a is secured to pole 104 above fixed member 130 and locking mechanism 160b is secured to pole 104 below fixed member 130. Referring to FIG. 1B, locking mechanism 160a has a first section 162a having the same configuration as the outer perimeter of pole 104, but is sized to tightly fit about pole 104. Locking mechanism 160a transitions through a necked down portion to a second section 164a, which releasably holds one end portion of cylindrical lever arm 142. Section 164a has a first portion having a configuration corresponding to the cross-section of lever arm 142, a second necked down portion and open portion for receiving or releasing lever arm 142. Locking mechanism 160a comprises a material that allows the open end portion to expand and then return toward its unexpanded shape so that it can be releasably secured to pole 104 and lever arm can be releasably locked in locking mechanism 160a. One suitable material is spring steel. The first portion can be sized to provide a secure clamp to pole 104 and prevent the locking mechanism from falling down the pole as would be apparent to one of ordinary skill. Locking mechanism 160b has the same construction as locking mechanism 160a.

Referring to FIG. 2, one leg configuration is shown. In this embodiment, adjacent legs 114a and 114d radially extend from pole 104 or hub 112. In contrast, adjacent legs 114b and 114c have first portions 115b1 and 115c1 that radially extend from pole 104 or hub 112, second portions 115b2 and 115c2 that extend in directions opposite one another after a bend, and third portions 115b3 and 115c3, which are substantially parallel to one another after another bend to accommodate a patient using the stand for support, while walking between leg portions 115b3 and 115c3 in the direction of arrow A1 or A2. This configuration also enables the patient to stand close to IV stand pole 104 and hold the pole for support. The patient can walk with a full stride without having the retractable legs 114a-d interfere with the patient's footsteps. The distance "X" between leg portions may vary depending on the size and stride of the patient. Typically, this distance will be about 32 inches to about 36 inches, and more typically about 36 inches.

Opposite leg pairs also can be dimensioned to further enhance stand stability when the patient holds pole 104. Referring to FIG. 2, leg pairs 114b,c and 114a,d are dimensioned so that wheels 116b and 116c are farther from support pole 104 than wheels 116a and 116d. In the illustrative embodiment, the distance D2 between a line L3, which passes through the center of wheels 116b and 116c, and a line L2, which passes through the longitudinal axis or centerline of support pole 104 and is parallel to line L2 (the distance being measured in a plane parallel to or coplanar with the plane upon which the wheels are supported), is greater than the distance D1 between a line L1, which passes through the center of wheels 116a and 116d and L2 (the distance being measured in a plane parallel to or coplanar with the plane upon which the wheels are supported). In one example, D1 is about 8 inches and D2 about 24 inches. The dimensions are selected to provide sufficient stability, while allowing the stand to pass through most doorways.

Referring to FIG. 2A another leg configuration is shown. In this embodiment, all of the legs radially extend from pole 104 or hub 112. However, legs 214b and 214c extend radially farther from pole 104 or hub 112 than legs 214a and 214d to provide a large span between wheels 216b and 216c as compared to the span between wheels 216a and 216d and to accommodate a patient using the stand for support, while walking in the direction of either arrow A1 or A2. Wheels 208a-d have the same construction as wheels 108a-d and wheels 216a-d have the same construction as wheels 116a-d. The other components are of the same construction as well. However, without similar leg portions 115a2 and 115a3 and leg portions 115c2 and 115c3, the distance between wheels 216b and 216c would be greater to accommodate the patient's stride as noted above. Alternatively, the coupling between each leg 214a-d and a respective wheel 216a-d is sized or the configuration of the end of each leg 214a-d is configured so that the radially extending portions of the legs are sufficiently above floor surface S (see e.g., FIG. 3D), for example, about 8-12 inches above the floor surface, so as to minimize or eliminate interference with the patient's feet when wheels 216a-d are in contact with floor surface S (see e.g., FIG. 3D). Further, this alternative height configuration can be combined with the increased distance between wheels 216b and 216c arrangement described above.

The following is set forth merely as an example to illustrate use of an adjustable stand constructed according to one embodiment of the invention and is not intended to limit the scope of the invention. For purposes of this example, the method will be described with reference to adjustable stand 100.

FIGS. 3A-3D diagrammatically illustrate conversion or adjustment of the IV stand from a compact configuration to a configuration suitable for use as a support to assist an ambulatory patient with walking, while coupled to an IV bag or container hung from the IV stand. FIG. 3A shows a side elevational view of the IV stand self-supported through a group of floor engaging wheels (wheels 108c and 108d are hidden from view), which engage floor surface S and are coupled to base member 102, and with its secondary or retractable wheels (wheels 116c and 116d are hidden from view) in a raised non-floor engaging position. FIG. 3B shows the secondary or retractable wheels being lowered. FIG. 3C shows another stage of the secondary or retractable wheels being further lowered. FIG. 3D shows the secondary wheels fully lowered and engaging floor surface S to support the IV stand, the base member wheels lifted so as to be non-floor engaging wheels, and the wheelbase expanded to increase stability of the IV stand. The height of the vertical portions of the retractable legs is greater than the combined height of the base member and its support wheels 108a-d so that the base member wheels are lifted off of floor surface S when the retractable legs are lowered into engagement with floor surface S. The raising of wheels 108a-d further minimizes interference with the patient's walking and/or reduces rolling resistance.

When the retractable legs are lowered, they increase the span of the IV stand support and enhance stand stability. And when the retractable legs are raised or retracted, the IV stand has a more compact configuration suitable for being stationed near the patient's bed and minimizing interference with medical staff.

Referring to FIG. 4, another adjustable IV stand embodiment generally designated with reference numeral 300 is shown. IV stand 300 is the same as IV stand 100 with the exception that base member 302 is thinner than base member 102 so that all of the base member wheels and retractable leg wheels remain engaged with the floor surface when the retractable legs are lowered. Accordingly, elements 304, 306, 308*a,b*, 310*a,b*, 314*a,b*, 316*a,b*, 318*a*, and 324*a,b* are the same as elements 104, 106, 108*a,b*, 110*a,b*, 114*a,b*, 116*a,b*, 118*a*, and 124*a,b*.

Any feature described in any one embodiment described herein can be combined with any other feature of any of the other embodiments whether preferred or not.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto.

What is claimed is:

1. An adjustable IV stand comprising:
    a base member having an upper surface and a lower surface and a plurality of rotating wheels non-pivotally coupled to said lower surface;
    a support pole for supporting an IV fluid container, said support pole having an upper end and a lower end, said lower end being coupled to said upper surface of, and supported by, said base member; and
    at least three swiveling wheels pivotally coupled to at least one of said support pole at said lower end and said base member on or above said upper surface, said swiveling wheels being adjustable between a raised non-floor engaging position and a lowered floor engaging position relative to said base member;
    wherein said base member wheels each have a lower surface in a first plane and said at least three swiveling wheels each have a lower surface in a second plane that is lower than said first plane when said at least three swiveling wheels are adjusted to said lowered position, such that when said when said at least three swiveling wheels are in the raised non-floor engaging position, said rotating wheels can engage and roll upon floor surface, and when said at least three swiveling wheels are in the lowered floor engaging position, said rotating wheels disengage from contact with a floor surface.

2. The adjustable IV stand of claim 1 further including first, second and third legs pivotally coupled to at least one of said support pole and said base member for adjustment between a raised position and lowered position relative to said base member, a first one of said swiveling wheels being coupled to said first leg, a second one of said swiveling wheels being coupled to said second leg, and a third one of said swiveling wheels being coupled to said third leg.

3. The adjustable IV stand of claim 1 further including a plurality of legs, each pivotally coupled to at least one of said support pole and said base member for adjustment between a raised position and lowered position relative to said base member, said swiveling wheels being coupled to said legs.

4. The adjustable IV stand of claim 1 wherein said base member wheels each have a lower surface in a first plane and said adjustable leg wheels each have a lower surface in a second plane that is not coplanar with said first plane when said adjustable legs are adjusted to said lowered position.

5. The adjustable IV stand of claim 1, wherein each of said at least three swiveling wheels are pivotally coupled to at least one of said support pole or said base member through an adjustable leg.

6. The adjustable IV stand of claim 5, wherein there are four of said adjustable legs.

7. The adjustable IV stand of claim 6, wherein when said adjustable legs are in said lowered position, two of said legs are spaced from said pole a distance greater than the distance between either of the other two legs and said pole.

8. The adjustable IV stand of claim 5, wherein there are four adjustable legs and two of said adjustable legs each have an end portion, said end portions being substantially parallel to one another.

* * * * *